US00PP14269P29

(12) United States Plant Patent
Strope

(10) Patent No.: US PP14,269 P2
(45) Date of Patent: Nov. 4, 2003

(54) ARGYRANTHEUM PLANT NAMED 'BALARGLUITE'

(50) Latin Name: *Argyranthemum frutescens*
Varietal Denomination: Balargluite

(75) Inventor: Kerry M. Strope, Jefferson City, MO (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/329,802

(22) Filed: Dec. 26, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Wood, Phillips, Katz, Clark & Mortimer

(57) ABSTRACT

A new and distinct Argyranthemum plant named 'Balargluite', characterized by its white ray florets, yellow disc florets, medium green foliage and upright growth habit.

2 Drawing Sheets

Latin name of the genus and species of plant claimed: *Argyranthemum frutescens.*
Variety denomination: 'Balargluite'.

BACKGROUND OF THE INVENTION

The present invention comprises a new and distinct Argyranthemum plant, botanically known as *Argyranthemum frutescens*, and hereinafter referred to by the name 'Balargluite'.

The new cultivar originated from a controlled breeding program with the objectives of developing Argytanthemem plants that are freely branching, freely flowering and have a compact, upright growth habit.

The new cultivar is the result of open pollination, with the female parent being a proprietary breeding selection designated NC2306, characterized by white flowers with yellow centers. The new cultivar was discovered by the inventor during February 2000, in a controlled environment at Arroyo Grande, Calif.

Asexual reproduction of the new cultivar has been carried out at Arroyo Grande, Calif. and West Chicago, Ill. by terminal tip cuttings and has demonstrated that the characteristics of the new cultivar as herein described are firmly fixed and retained through successive generations of such asexual propagation.

SUMMARY OF THE INVENTION

It was found that the cultivar of the present invention:

(a) exhibits white ray florets with light yellow disc florets, (b) forms medium green foliage, (c) a good basal branching character, and (d) exhibits a compact upright growth habit.

The new cultivar of the present invention can be compared to 'Sugar Baby' (U.S. Plant Pat. No. 10,298). In side-by-side comparisons, plants of the new cultivar have larger leaves and larger flowers with fewer ray florets.

BRIEF DESCRIPTION OF PHOTOGRAPH

The accompanying photographs show as nearly true as it is reasonably possible to make the same in color illustrations of this type, typical flower and foliage characteristics of the new cultivar. Colors are as accurately represented as can be made by conventional photography. The plants were grown in 10 m cm pots for 10 weeks in a greenhouse at West Chicago, Ill.

DETAILED BOTANICAL DESCRIPTION

Figure 1:
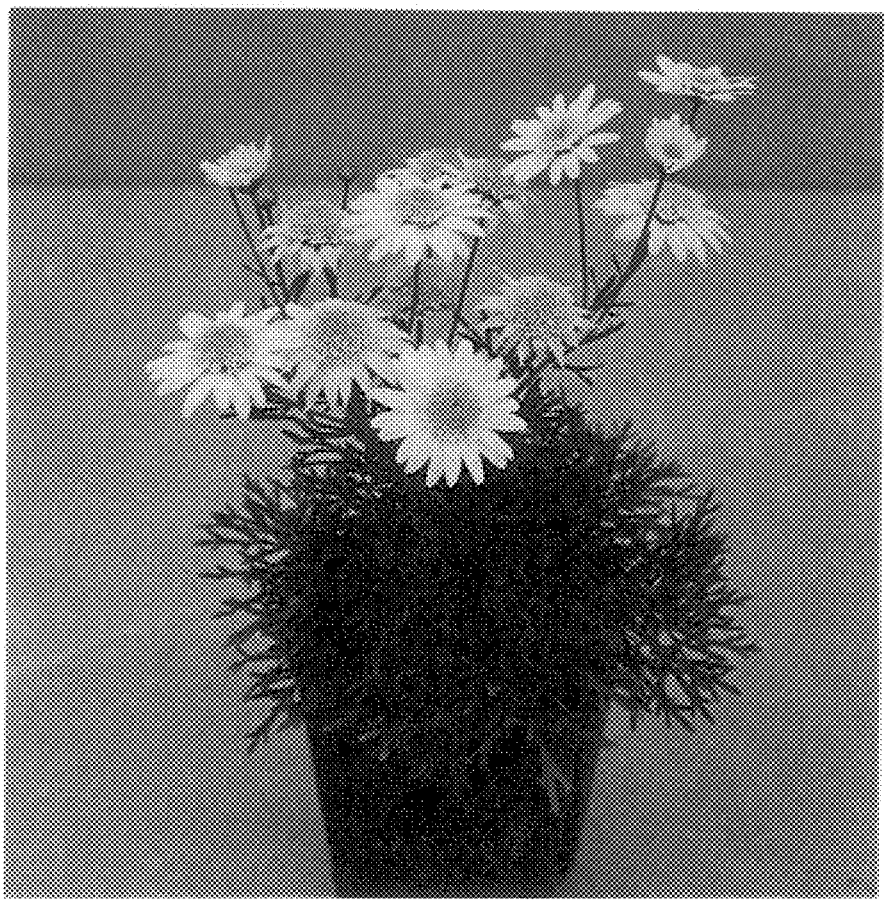
FIG. 1 illustrates the overall growth habit of the new cultivar with one plant per pot.
Figure 2:
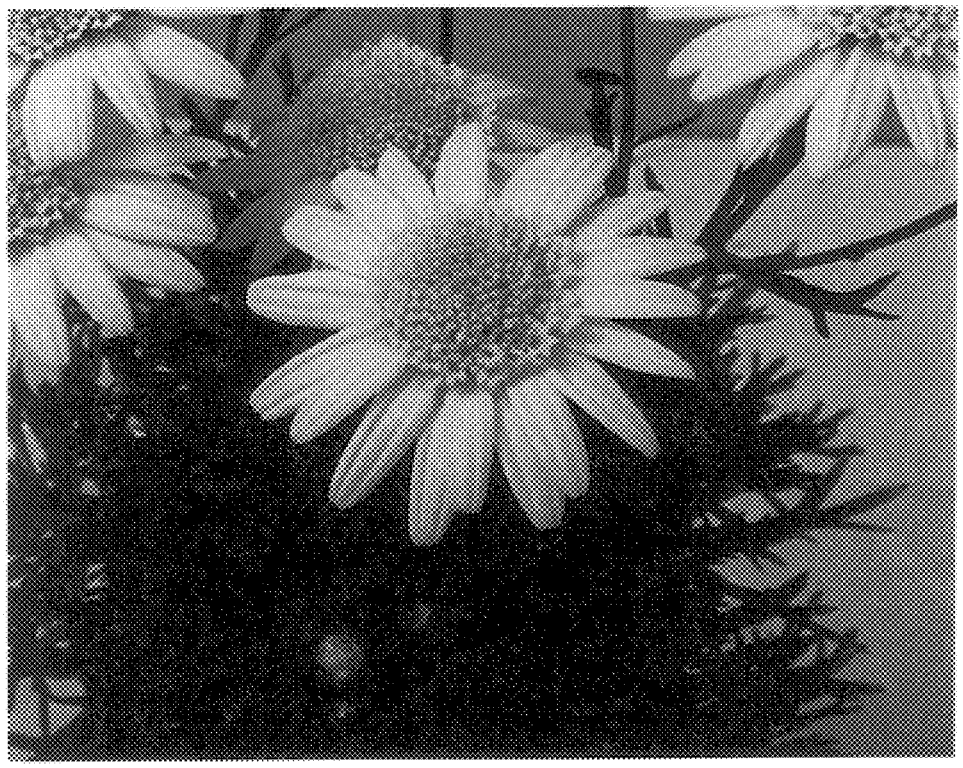
FIG. 2 illustrates a close-up of individual flowers of the new cultivar.

The new cutivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 17, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown utilizing a soilless growth medium and maintaining temperatures of approximately 65° to 78° F. (18° to 25° C.) during the day and approximately 50° to 60° F. (10° to 15° C.) during the night and light levels of 6,000 to 9,000 footcandles. Plants used for the following descriptions and measurements were grown in 10 cm pots for 10 weeks from rooted cuttings.

Classification:
*Botanical.*—*Argyranthemum frutescens* cultivar 'Balargluite'.
Parentage:
*Female parent.*—Proprietary breeding selection NC2306.

Propagation:

*Type cutting.*—Terminal tip.

*Time to initiate roots.*—Approximately 7 to 10 days.

*Time to develop roots.*—Approximately 14 to 21 days.

*Root description.*—Fibrous, branching.

Plant description:

*Crop time.*—Approximately 8 weeks in a 10 cm pot.

*Habit of growth.*—Compact. Freely branching. One or two pinches improves basal branching.

*Form.*—Upright, mounded.

*Plant height.*—A mature plant, 10 weeks after the planting of a rooted cutting, commonly measures approximately 19.8 cm.

*Plant diameter.*—Approximately 17.4 cm.

*Branch.*—Texture: Glabrous. Color: 145B with spots of 77A. Internode length at middle of branch: Approximately 1.4 cm.

*Foliage.*—Leaves are non-fragrant, single, alternate and at an acute angle to the stem. Shape: Pinnatified. Margin: Entire. Apex: Acute. Base: Sessile, clasping. Upper and lower surfaces are glabrous. Leaf length: Approximately 5.6 cm. Leaf width: Approximately 3.5 cm. Leaf color: Upper surface of mature foliage is 144A, lower surface of mature foliage is 144A. Both upper and lower surfaces have venation closest to 144C.

Flowering description:

*Flowering habit.*—Freely flowering.

*Natural flowering season.*—Year round in greenhouse environment and spring through autumn in outdoor garden.

*Inflorescence type.*—Single composite. Persistent.

*Inflorescence description.*—Shape: Round. Diameter: Approximately 4 cm. Depth: Approximately 9 mm. Aspect: Facing upward or outward. Fragrance: None. Number per plant: Approximately 7.

*Ray florets.*—Number: Approximately 16. Aspect: Flat to slightly concave. Texture: Glabrous and ribbed. Arrangement: Very slightly overlapping. Shape: Oblong. Margin: Entire. Tip: Emarginate. Base: Attenuate and fuse to form tube. Width: Approximately 3 mm. Length: Approximately 1.2 cm. Color: Upper and lower surfaces: 155D. Tube at base is pubescent and N144A.

*Disc.*—Diameter: Approximately 1.9 cm. Depth: Approximately 6 mm. Number of disc florets: Approximately 143.

*Disc florets.*—Shape: Tubular with five lobes. Margin: Entire. Texture: Glabrous. Length: Approximately 6 mm. Width: Approximately 3 mm.

*Phyllaries.*—Approximately 30, imbricate, arranged in several rows. Length: Approximately 4 mm. Width: Approximately 4 mm. Shape: Ovate. Color of upper surface: Closest to 145C. Color of lower surface: Closest to 145D.

*Peduncle.*—Strong, glabrous, at an acute angle to the stem. Length: Approximately 5.2 cm. Diameter: Approximately 1 mm. Color: 144B.

*Bud.*—Round, approximately 5 mm in length and 6 mm in diameter. Bud color is 165B.

*Reproductive organs.*—Androecium: Present on disc florets only. Stamens: 4. Anthers are less than 1 mm in length. Pollen amount: Moderate. Pollen color: 4C. Gynoecium: Present on ray and disc florets. There is one pistil per floret. Pistil length: 2 mm. Stigma shape: two parted. Stigma length: 1 mm. Stigma color: 150C. Style length: Less than 1 mm. Style color: 144C. Ovary diameter: Less than 1 mm. Ovary color: 144C.

Seed production: Seed production has not been observed.

Disease resistance: Resistance to pathogens has not been observed.

Hardiness zone: 'Balargluite' is hardy in zones nine (9) and above.

I claim:

1. A new and distinct Argyranthemum plant named 'Balargluite' substantially as herein shown and described, which:

(a) exhibits white flowers with light yellow centers, (b) medium green foliage, (c) a good basal branching character and (d) a compact upright growth habit.

* * * * *